United States Patent [19]

MacAllister

[11] Patent Number: 5,016,614
[45] Date of Patent: May 21, 1991

[54] ENDOTRACHEAL INTUBATION APPARATUS

[76] Inventor: Niall P. MacAllister, Rte. 1, Box 473, Cooper Road, Eden, Md. 21822

[21] Appl. No.: 52,138

[22] Filed: May 4, 1987

Related U.S. Application Data

[63] Continuation of Ser. No. 796,321, Nov. 7, 1985, abandoned, which is a continuation of Ser. No. 407,143, Aug. 11, 1982, abandoned.

[51] Int. Cl.$^5$ .............................................. A61B 1/00
[52] U.S. Cl. ............................................. 128/4; 128/6; 128/207.11; 604/93; 604/119
[58] Field of Search ............... 128/207.14, 207.15, 128/207.18, 204.18, 200.26, 207.16, 265.11, 204.21, 912, 4, 6, 8, 10, 11, 16; 604/93, 95, 119, 43

[56] References Cited

U.S. PATENT DOCUMENTS

| | | | |
|---|---|---|---|
| 2,433,705 | 12/1947 | Palmeter | 128/16 |
| 2,918,917 | 12/1959 | Emerson | 128/604.21 |
| 3,091,235 | 5/1963 | Richards | 128/6 |
| 3,373,736 | 3/1968 | Fiore et al. | 128/6 |
| 3,677,262 | 7/1972 | Zukowski | 128/6 |
| 3,709,214 | 1/1973 | Robertson | 128/6 |
| 3,726,272 | 4/1973 | Fukami et al. | 128/6 |
| 3,776,222 | 12/1973 | Smiddy | 604/95 |
| 3,830,225 | 8/1974 | Shinnick | 128/4 |
| 3,850,162 | 11/1974 | Iglesias | 128/6 |
| 3,913,568 | 10/1975 | Carpenter | 128/11 |
| 3,916,881 | 11/1975 | Heine | 128/16 |
| 3,941,120 | 3/1976 | Lee | 128/8 |
| 4,126,127 | 11/1978 | May | 128/11 |
| 4,146,019 | 3/1979 | Bass et al. | 128/6 |
| 4,270,575 | 6/1981 | Furihata | 604/119 |
| 4,344,419 | 8/1982 | Burgin | 128/3 |
| 4,402,310 | 9/1983 | Kimura | 128/6 |
| 4,408,598 | 10/1983 | Ueda | 128/4 |
| 4,517,962 | 5/1985 | Heckele | 128/6 |
| 4,616,630 | 10/1986 | Arakawa | 128/4 |
| 4,617,915 | 10/1986 | Arakawa | 128/4 |

FOREIGN PATENT DOCUMENTS 2167010 7/1977 Fed. Rep. of Germany .......... 128/6

Primary Examiner—Randall L. Green
Assistant Examiner—K. Reichle
Attorney, Agent, or Firm—Sachs & Sachs

[57] ABSTRACT

A medical instrument for facilitating endotracheal intubation in a patient, the instrument including a handle and an elongated obturator element extending therefrom, the obturator element for releasably retaining thereon a selected endotracheal tube for positioning within the patient, a mechanism being provided for selectively retaining and ejecting the endotracheal tube from the obturator element, the obturator element accommodating therethrough an endoscope to permit visualization at the end thereof to facilitate placement of the endotracheal tube, the apparatus also including structure for providing controlled suction at the end of the obturator element.

30 Claims, 2 Drawing Sheets

ENDOTRACHEAL INTUBATION APPARATUS

CROSS REFERENCE TO RELATED APPLICATION

This is a continuation of co-pending application Ser. No. 796,321 filed on Nov. 7, 1985, now abandoned.

That application is a continuation of application Ser. No. 407,143, filed on Aug. 11, 1982, now abandoned.

BACKGROUND OF THE INVENTION

1. Field of the Invention

The present invention relates to apparatuses for endotraceal intubation, and more particularly to a medical instrument which facilitates endotracheal intubation by simultaneously providing visualization of the intubation as well as controlled delivery of gas and suction at the end of an obturator which carries the endotracheal tube.

2 Description of the Prior and Contemporary Art

Endotracheal intubation is a medical procedure which concerns the placement of a tube in the trachea of a patient to facilitate breathing or to permit the controlled introduction of certain gasses through the tube by an anesthesiologist, or other medical personnel for appropriate purposes. In the past, endotracheal intubation only has been attempted and accomplished under controlled circumstances which were not acute, i.e., where no immediate medical emergency existed. For instance, uncuffed tracheotomy tubes were used to provide an airway in patients during the Scandinavian polio epidemic of 1952. Unfortunately, the use of these essentially plain tubes was not particularly successful and the mortality rate was approximately eighty percent at the beginning of the use of the tubes. By using a cuffed endotracheal tube and a proper ventilator in conjunction with the tube, the mortality rate was lowered to approximately thirty percent.

In the midfifties, a branch of medicine called "critical care medicine" began to develop. Critical care medicine is concerned with treatment of acute patients who have been the victims of serious accidents or the like. To cater to critical care patients, intensive care units have been opened in many hospitals. For instance, the intensive care unit at Baltimore City Hospital opened in 1958 and the intensive care unit opened at Massachusetts General Hospital in 1961. Typically, the patients in these units are critically ill following surgery, accident induced trauma, or acute infectious processes.

Trauma is the leading cause of death in the U.S. in patients between the ages of one and forty. Twenty million people will seek emergency room treatment this year, over one hundred and fifty thousand of whom will die from their injuries. A common type of trauma is face trauma wherein the airway function of the patient is compromised. This causes the aspiration of blood or vomitus and results in ventilatory or pulmonary complications. As a result, the most common causes of trauma related deaths are inadequate ventilation, inadequate circulation, or more massive hemorrhage for which there is little recourse. As critical care medicine developed, acute resuscitation techniques were established. Respiratory resuscitation started developing in the 1950's. External cardiac and cardo-pulmonary resuscitation developed in the 1960's. Proper ventilation is critical as pointed out by Doctors Weil and Shubin, former Directors of intensive care at the University of California and the founders of the Society of Critical Care Medicine. The doctors stated that the first priority among the primary functions which determine survival in all critical care units is the maintenance of ventilation and gas exchange.

Despite this development in critical care medicine, no heretofore satisfactory method of ventilation has been developed and despite the recognition of the importance of maintaining ventilation and gas exchange, devices known in the prior art have not satisfactorily accomplished this task. In Vietnam, for example, asphyxiation from upper airway obstruction or injury was a common cause of death in the field or enroute to forward surgical facilities.

It therefore can be concluded that priorities in critical care medicine must respond to airway management, breathing and circulatory problems and that the efficiency of airway management is essential to optimal circulatory resuscitation. Unfortunately, hardware development in this area has been virtually arrested in terms of development of a single instrument which can provide all the necessary functions. No instrument presently available provides visualization of the airway and airway access in acute resuscitation, the ability to suck debris to avoid aspiration and to assist in obtaining visualization, means for providing ventilation capabilities and also means for carrying and inserting a suitable airway tube in position. Presently, in order to obtain and maintain a properly functioning airway, at least two instruments are required for placement of an endotracheal tube, unless blind insertion of the tube is attempted. The blind insertion of the tube, that is the placement of a tube on a suitable obturator and the insertion of the obturator without visualization, leads to numerous lethal complications. Specifically, the location and passage of the tube cannot be visualized and there is no way to provide ventilation, the much needed reason for placing the tube to begin with, while the tube is being positioned. In some instances, placement of a tube has been enhanced by the use of a laryngoscope which permits entry of the tube and an obtruator which includes an optical stylet for introducing the tube. The use of a laryngoscope along with an obturator and an optical stylet or endoscope requires multi-handed, complicated manipulation of several instruments at once with the critically situated patient being the loser for the inefficiency of such procedures.

Specifically surveying the prior art, a larynogoscope with illumination means is shown in U.S. Pat. No. 2,646,036 and an endoscope with illumination means can be found in U.S. Pat. No. 3,269,387. Intubating stylets, i.e., fixtures for carrying thereon tubes to facilitate the insertion thereof, can be found in U.S. Pat. Nos. 2,463,149 and 2,541,402. Bronchoscopy tubes which permit delivery of a fluid or oxygen during use are shown in U.S. Pat. Nos. 4,041,936; 3,941,120; 3,850,162; 3,460,541; 3,348,542; 3,175,557; 2,705,959; 4,090,518; and 4,146,019. U.S. Pat. Nos. 2,912,982 and 3,087,493 teach endotracheal tubes which permit gas suctioning and gas delivery.

Surgical endoscopes which provide illumination means in addition to a telescope and which in some instances provide for the delivery of fluids or suction are shown in U.S. Pat. Nos. 3,830,225; 3,572,325; 3,162,190; 2,704,541; and 2,129,391. None of these devices, however, show or suggest the use of an endotracheal tube therewith and each of these apparatuses can only accomplish its function when in position, with tubal ventilation upon removal not being possible.

U.S. Pat. No. 3,147,746 teaches an illuminating endoscope which permits intubation, but does not permit simultaneous use of an obturator and visualization. As a result, the obturator is used to place the device in position and only then can visualization take place after the obturator is removed.

A similar apparatus wherein an obturator must be removed from a tube so that visualization by a scope can take place is shown in U.S. Pat. No. 3,081,767.

U.S. Pat. No. 3,677,262 shows a surgical instrument which permits endotracheal intubation simultaneously with visualization. No means are shown or suggested for accomplishing ventilation during intubation nor are means shown or suggested for selectively retaining and/or ejecting the tube during the intubation process.

After reviewing the aforegoing, it is obvious that there has been quite a bit of activity in the field of endotracheal intubation. Nonetheless, no one heretofore has provided an apparatus which integrates all the necessary and desirable features into a single instrument which accomplishes intubation in a safe and optimumly fast way despite all the activity in this area and recent growing emphasis in critical care medicine.

Despite this intense emphasis on critical care medicine since the early 1970's, no one has developed an integrated instrument for safely and quickly placing an endotracheal tube. With this as a backdrop, the present invention overcomes the shortcomings of the prior art by providing a medical instrument for facilitating endotracheal intubation or the like which, in a single integrated, apparatus, provides light and visualization for placement of an endotracheal tube, an obturator for support of the endotracheal tube, suction to enhance visualization and to preclude asphyxiation, and a ventilation source so that rapid airway gas exchange can take place. All this has been integrated into a single instrument which can be used with one hand providing for "fast" in and out so that the maximum number of patients can be aided with the lowest possible morbidity.

SUMMARY OF THE INVENTION

Therefore, a primary object of the present invention is to provide a medical instrument for facilitating endotracheal intubation.

A further object of the present invention is to provide a medical instrument for facilitating endotracheal intubation which permits rapid, successful, and nonlethal intubation to be accomplished.

A still further object of the present invention is to provide a medical instrument for facilitating endotracheal intubation wherein the intubation is visualized while being effected.

Still another object of the present invention is to provide a medical instrument for facilitating endotracheal intubation wherein ventilation can be accomplished as intubation is taking place.

Still another further object of the present invention is to provide a medical instrument for facilitating endotracheal intubation wherein suction is provided during intubation to enhance visualization and to preclude lethal aspiration of blood or vomitus.

Another further object of the present invention is to provide a medical instrument for facilitating endotracheal intubation which accomplishes all the aforenoted objects and is embodied in a single instrument which can be handled by a physician in one hand.

Another still further object of the present invention is to provide an endotracheal intubation instrument which provides means for securing the endotracheal tube until it is in position and also provides means for ejecting the endotracheal tube once it is in position.

An additional object of the present invention is to provide a medical instrument for facilitating endotracheal intubation which is compatible with presently known ventilation devices.

A still additional object of the present invention is to provide a medical instrument for facilitating endotracheal intubation which is simple in design, inexpensive to manufacture, rugged in construction, easy to use, and efficient in operation.

These objects, as well as further objects and advantages of the present invention, will become readily apparent after reading the ensuing description of several nonlimiting illustrative embodiments and reviewing the accompanying drawings.

A medical instrument for facilitating endotracheal intubation or the like in a patient, according to the principles of the present invention, includes a handle adapted to be gripped by the user physician; an elongated obturator element fixedly secured adjacent to a first end thereof to the handle, the obturator element for releasably retaining thereon a selected endotracheal tube, the obturator element having a longitudinal lumen disposed therein which extends from the first end of the obturator to the second end thereof, the longitudinal lumen adapted to removably receive therein a portion of an endoscope to permit visualization by the endoscope at the second end of the obturator element; means for selectively retaining and ejecting a selected endotracheal tube when associated with the obturator element; means for providing controlled delivery of gas to the second end of the obturator element; and means for providing controlled suction at the second end of the obturator element.

BRIEF DESCRIPTION OF THE DRAWINGS

In order that the present invention may be more fully understood, it will now be described, by way of example, with reference to the accompanying drawings in which.

DESCRIPTION OF THE PREFERRED EMBODIMENTS

Figure 1:
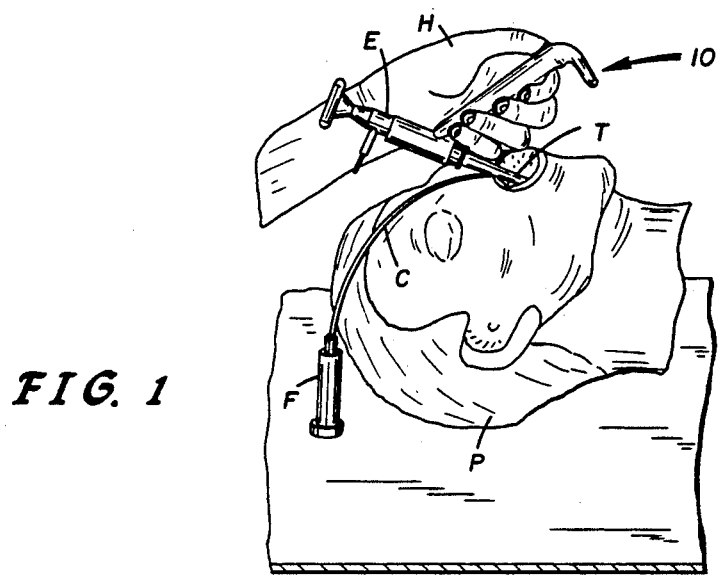
FIG. 1 is a pictorial representation of the medical instrument incorporating the principles of the present invention in use in placement of a tube in a patient.

Referring now to the figures, and more particularly to FIG. 1 thereof, there is illustrated a medical instrument 10 which incorporates the principles of the present invention therein. The instrument 10 is illustrated in use in carrying out an intubation procedure in a patient P, the instrument 10 being held by the hand H of a physician, not illustrated. Disposed on the instrument 10 is an endotracheal tube T having a fixture F for attachment to a cuff inflation apparatus, well known in the art, fixture F being coupled to the tube T by a conduit C. Disposed within the instrument 10 is an endoscope E, as hereinafter further described. Although an endoscope E is illustrated, it is to be understood that other types of medical visualization scopes sometimes called telescopes, bronchoscopes, or the like can also be employed.

Figure 2:
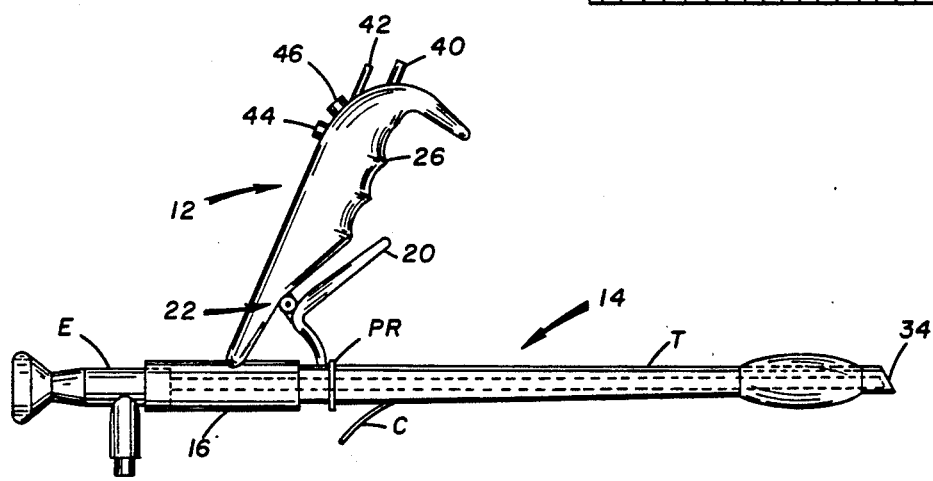
FIG. 2 is a pictorial representation of the instrument in use in FIG. 1.
Figure 4:
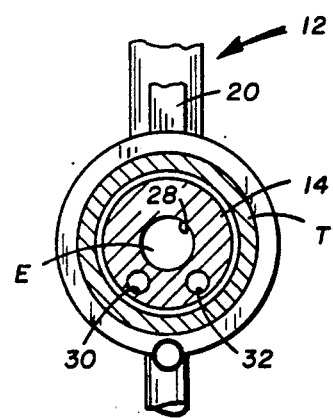
FIG. 4 is a cross sectional view taken substantially through the lines 4—4 of FIG. 3.
Figure 3:
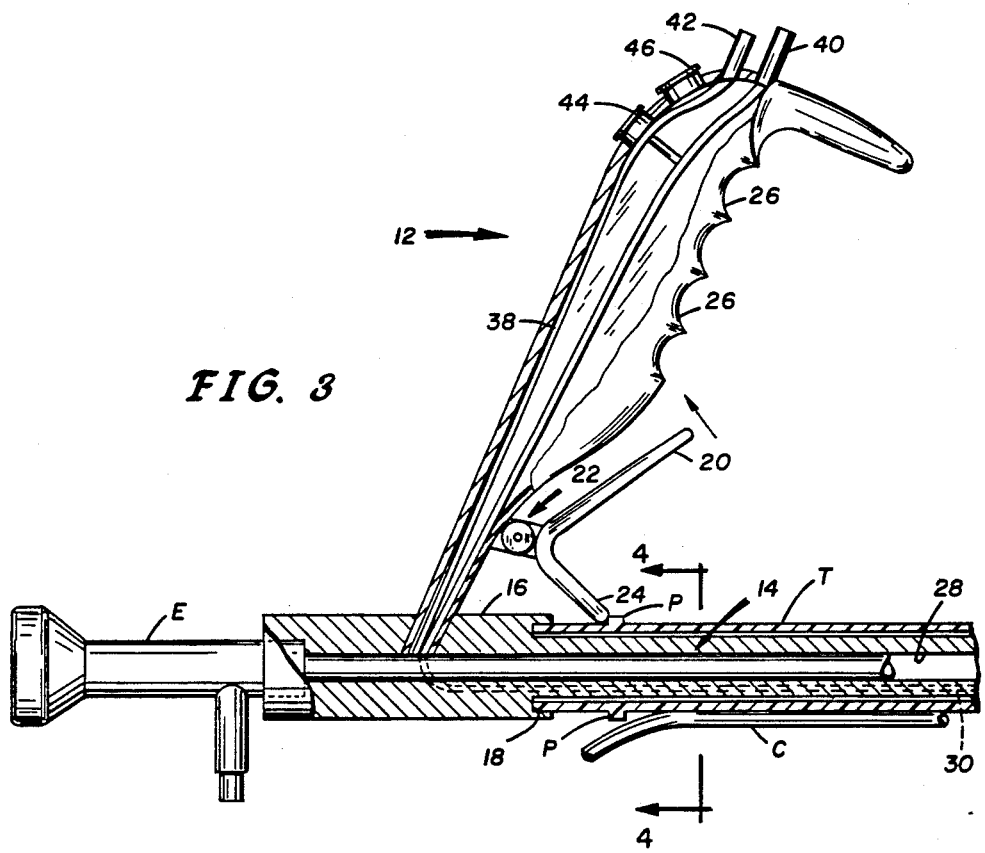
FIG. 3 is an enlarged fragmentary partially broken away view of the instrument of FIG. 2.

With reference to FIGS. 2, 3, and 4, the structure of the instrument 10 can be observed. The instrument 10 includes a handle 12 which is fixedly secured to an elongated obturator element 14. The elongated obturator element 14 is sized to accommodate the endotracheal tube T thereon and includes a collar portion 16 for frictionally engaging the end of the endotracheal tube T. The collar portion 16 has an annular recess 18 formed therein for engaging the end of the endotracheal tube T with an annular recess 18 being sized to cause frictional engagement. A trigger 20, which essentially functions as a lever, is pivotably mounted by a pivot mounting 22 to the handle 12. An end 24 of trigger 20 is shaped so that it engages a protrusion PR, commonly annular in shape, disposed on the endotracheal tube T adjacent to the end thereof. When the trigger 20 is drawn by the user toward the handle 12, the end 24 of the trigger 20 pushes the protrusion PR overcoming the frictional engagement between the endotracheal tube T and the collar 16, thereby causing the endotracheal tube to be forced out of engagement with the collar portion 16 and causing the endotracheal tube to be ejected from the elongated obturator element 14.

The handle 12 includes a plurality of undulations 26 to enhance the comfort of the handle 12 in the hand H of the physician, as illustrated in FIG. 1, and the trigger 22 is placed in a position relative to the undulations 26 so that it is readily accessible to the physician.

The elongated obturator element 14 has a longitudinal lumen 28 disposed therein which is sized to removably receive therein a portion of the endoscope E, as illustrated in FIGS. 3 and 4. Also disposed longitudinally in the elongated obturator element 14 are a longitudinal gas delivery lumen 30 and a longitudinal suction lumen 32 which each terminate and open through the end 34 of the elongated obturator element 14. The longitudinal gas lumen 30 and the longitudinal suction lumen 32 are in communication, respectively, with conduits 36 and 38 disposed in the handle 12 of the instrument 10. The conduits 36 and 38 terminate, respectively, in fittings 40 and 42 which are configured to affix to a conventional gas supply and suction apparatus, an example of which is the Sanders Venturi system. Alternately, one of the other numerous high frequency ventilation systems used in resuscitation and endoscopic procedures can be employed.

A pair of vents 44 and 46 are in communication, respectively, with the conduits 36 and 38 and are mounted on the handle 12. The fittings 40 and 42, vents 44 and 46, and the conduits 36 and 38 can be integrally formed with the handle 12 or can be incorporated therein from separate components during manufacture. The vents 44 and 46 are provided to control, respectively, the delivery of gas through the longitudinal gas lumen 30 and the provision of suction to the longitudinal suction lumen 32.

When the vents 44 and 46 are uncovered, nothing is delivered or suctioned from the end 34 of the elongated obturator element 14. If the vent 44 is covered by a finger of the physician, gas, usually oxygen, which must be supplied to the patient, is not permitted to exit the vent 44 and is forced through the conduit 36 to the longitudinal gas lumen 30 and out the end thereof. When the finger is removed from the vent 44, the gas does not flow through the longitudinal gas lumen 30 and escapes through the vent 44.

By covering the vent 46, suction is created in the conduit 38, by virtue of a suitable suction source being connected to fitting 42, and this causes suction to also be created in the longitudinal suction lumen 32. When the vent 46 is uncovered, the suction in the conduit 38 and the longitudinal suction tube 32 is terminated since atmospheric air can be sucked in through the vent 46. Although vents 44 and 46 are illustrated for modulating the delivery of gas and the provision of suction, it is to be understood that those skilled in the art could substitute alternate means for accomplishing this end.

What has been described is a medical instrument which permits simultaneous visualization and illumination, through use in conjunction with an endoscope, as well as suction, ventilation, and a support or obturator for the intubation of an endotracheal tube. This apparatus can be employed with the use of just one hand of a physician, all of these functions being accomplishable simultaneously. Furthermore, the endoscope can be interchanged or replaced as desired without removal of the instrument from its placement within a patient.

As illustrated in FIG. 1, when the instrument is held in a semi-vertical or suspension position it can provide anterior lift during intubation. Once the obturator element 14 of the apparatus is in position, the endotracheal tube or the like, which is to be left in the patient after the instrument 10 is withdrawn, is separated therefrom easily and quickly by pulling of the trigger 20 and the pivoting thereof, without the necessity of any more than a single handed operation.

Figure 5:
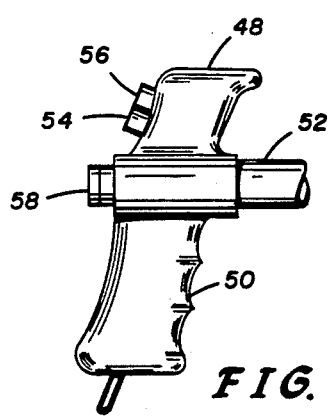
FIG. 5 is a fragmentary view of an alternate embodiment of the present invention.
Figure 6:
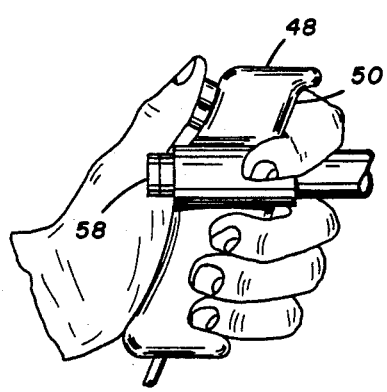
FIG. 6 is a pictorial representation of the embodiment of FIG. 5 in use.

An alternate embodiment of the present invention is illustrated in FIGS. 5 and 6. The variation in construction of this embodiment is in the handle portion of the apparatus and therefore that is the only section which is illustrated. In FIGS. 5 and 6, a handle 48 having suitable undulations 50 is shown fixedly secured to an elongated obturator element 52. The elongated obturator element 52 is mounted to the handle 48 intermediate the ends thereof so that the physician's hand, as illustrated in FIG. 6, can grip the handle with the elongated obturator element 52 suspended between the fingers of the hand H of the physician. A pair of vents 54 and 56 are provided and perform the same function as the vents 44 and 46, previously described. Similarly, an aperture 58 is provided, the aperture 58 being the end of a longitudinal lumen which extends through the elongated obturator 52 for accepting therein an endoscope.

A differently configured trigger 60 is incorporated in the handle 48 for separating therefrom the end of an endotracheal tube, the trigger 60 being mounted to the handle in the same pivotal relationship as is the trigger 20. This configuration is provided and suggested since it may be of a more comfortable arrangement for some of the required intubation positions. It is also to be understood that other modifications of the structure of the present invention and in particular in regard to the handle portion thereof may be made within the principles and scope of the invention. Additionally, locations of the vents can be such that they are disposed other than in the positions illustrated.

The apparatus hereinbefore described can find application in emergency resuscitation as a replacement for the much less sophisticated or dangerous esophageal obturator. In addition, it can be used as a temporary safe ventilation system at disaster scenes or in wartime positions in the field. In ear, nose, and throat medical practices, it may find use as an adjunct in endoscopic procedures and in the intensive care unit it can be employed for airway inspection and changing of endotracheal tubes or the like. In general, the apparatus will find use in the critical care endoscopy and maxillofacial surgery branches of medicine.

It will be understood that various changes in the details, materials, arrangements of parts and operational conditions, which have been herein described and illustrated in order to explain the nature of the invention, may be made by those skilled in the art within the principles and scope of the invention.

Having thus set forth the nature of the invention, what is claimed is:

1. A medical instrument for facilitating endotracheal intubation or the like in a patient by a selected endotracheal tube comprising:

handle means for gripping by one hand of a user;
   elongated obturator means having first and second ends and being fixedly secured adjacent to said first end thereof to said handle means, said obturator means for releasably retaining thereon a selected endotracheal tube, said obturator means having a longitudinal lumen disposed therein extending from said first end of said obturator means to said second end thereof, said obturator means also for removably receiving in said longitudinal lumen at least a portion of an endoscope thereby permitting visualization by said endoscope at said second end of said obturator means;
   means for selectively retaining and ejecting the selected endotracheal tube when disposed upon said obturator means;
   means for providing controlled delivery of a gas to said second end of said obturator means for supplying said gas to the patient for anesthetic and ventilation purposes as desired by the user; and
   means for providing controlled suction at said second end of said obturator means;
   wherein said selectively retaining and ejecting means, said controlled gas delivery means and said controlled suction means are controlled by the one hand of the user when said handle means is gripped by the one hand of the user.

2. A medical instrument in accordance with claim 1, wherein said selective retaining and ejecting means comprises means for frictionally retaining the selected endotracheal tube and means for overcoming said frictional engagement and simultaneously ejecting the endotracheal tube.

3. A medical instrument in accordance with claim 2, wherein said frictional engagement means comprises collar means mounted on said obturator means adjacent to said first end thereof, said collar means for engaging the end of the selected endotracheal tube which falls adjacent to said first end of said elongated obturator means when the selected endotracheal tube is disposed thereon.

4. A medical instrument in accordance with claim 2, wherein said friction overcoming and simultaneously ejecting means is a lever having one end thereof for engaging a portion of the selected endotracheal tube, said lever being pivotally affixed to said handle means, pivoting of said lever terminating retention of the selected endotracheal tube by said frictional engagement means.

5. A medical instrument in accordance with claim 4 wherein said lever is configured as a trigger.

6. A medical instrument in accordance with claim 2, wherein said selective retaining and ejecting means comprises frictional engagement means in the form of collar means mounted on said obturator means adjacent to said first end thereof, said collar means for engaging the end of the selected endotracheal tube which falls adjacent to said first end of said elongated obturator means when the selected endotracheal tube is disposed thereon, and frictional overcoming means being in the form of a lever having one end thereof for engaging a portion of the selected endotracheal tube, said lever being configured as a trigger and being pivotally mounted on said handle means, pivoting of said lever breaking frictional engagement between said collar means and the selected endotracheal tube and therefore terminating the retention thereof.

7. A medical instrument in accordance with claim 1, wherein said handle means includes a plurality of finger undulations to facilitate the grasping thereof by a user.

8. A medical instrument in accordance with claim 1, wherein said handle means comprises a first end and a second end, said elongated obturator means being fixedly secured to said first end of said handle means.

9. A medical instrument in accordance with claim 1, wherein said handle means comprises a first end and a second end, said elongated obturator means being fixedly secured to said handle means intermediate and spaced from the ends thereof.

10. A medical instrument in accordance with claim 1, wherein said controlled gas delivery means comprises a longitudinal gas delivery lumen having two ends and being disposed in said elongated obturator means such that said gas delivery lumen opens on one end thereof through said second end of said elongated obturator means, and means for a controlled supply of gas to the other end of said gas delivery lumen.

11. A medical instrument in accordance with claim 10, wherein said controlled gas supply means comprises a gas conduit having two ends and being in communication at one end thereof with said other end of said gas delivery lumen, the other end of said gas conduit for communicating with a supply of gas, and vent means intermediate said ends of said gas conduit, said vent means being configured such that said gas conduit is substantially precluded from delivering gas to said gas delivery lumen unless said vent means is closed.

12. A medical instrument in accordance with claim 11, wherein said other end of said longitudinal gas delivery lumen is disposed adjacent to said handle means, said gas conduit being disposed in said handle means and said vent means having an opening through said handle means.

13. A medical instrument in accordance with claim 12, wherein said vent means opening is defined by a finger receiving portion for closing by a finger of the user.

14. A medical instrument in accordance with claim 1, wherein said controlled suction means comprises a longitudinal suction lumen having two ends and being disposed in said elongated obturator means such that said lumen opens on one end thereof through said second end of said elongated obturator means, and means for controlled delivery of suction to the other end of said longitudinal suction lumen.

15. A medical instrument in accordance with claim 14, wherein said controlled suction delivery means comprises a suction conduit having two ends and being in communication at one end thereof with said other end of said suction lumen, the other end of said suction conduit for communicating with a suction apparatus, and vent means intermediate said ends of said suction conduit, said vent means being configured such that said suction conduit is substantially precluded from delivering suction to said suction lumen unless said vent means is closed.

16. A medical instrument in accordance with claim 15, wherein said other end of said longitudinal suction lumen is disposed adjacent to said handle means, said vent means has an opening through said handle means, and said suction conduit is disposed in said handle means.

17. A medical instrument in accordance with claim 16, wherein said vent means opening has a finger receiving portion for closing by a finger of the user.

18. A medical instrument for facilitating endotracheal intubation or the like in a patient by a selected endotracheal tube comprising:

handle means for gripping by one hand of a user, said handle means including a plurality of finger undulations to facilitate the grasping thereof by said user;

elongated obturator means having first and second ends and being fixedly secured adjacent to said first end thereof to said handle means, said obturator means for releasably retaining thereon a selected endotracheal tube, said obturator means having a longitudinal lumen disposed therein extending from said first end of said obturator means to said second end thereof, said obturator means also for removably receiving in said longitudinal lumen at least a portion of an endoscope thereby permitting visualization by said endoscope at said second end of said obturator means;

means for selectively retaining and ejecting the selected endotracheal tube when disposed upon said obturator means, said selective retaining and ejecting means including means for frictionally retaining the selected endotracheal tube and means for overcoming said frictional retaining means, said frictional overcoming means including collar means mounted on said obturator means adjacent to said first end thereof, said collar means for engaging the end of the selected endotracheal tube falling adjacent to said first end of said elongated obturator means when the selected endotracheal tube is disposed thereon, said frictional overcoming means including a lever having one end thereof for engaging a portion of the selected endotracheal tube, said lever being configured as a trigger and being pivotally mounted on said handle means, pivoting of said lever terminating retention of the selected endotracheal tube by said frictional retaining means;

means for providing controlled delivery of a gas to said second end of said obturator means as desired by a user, said controlled gas delivery means including a longitudinal gas delivery lumen having two ends disposed in said elongated obturator means such that said longitudinal gas delivery lumen opens on one end thereof through said second end of said elongated obturator means, said other end of said longitudinal gas delivery lumen being disposed adjacent to said handle means, and means for controlled supply of gas to the other end of said longitudinal gas delivery lumen, said controlled gas supply means including a gas conduit having two ends and being in communication at one end thereof with said other end of said longitudinal gas delivery lumen at the juncture of said handle means and said obturator means, the other end of said gas conduit for communicating with a supply of gas, and vent means intermediate said ends of said gas conduit and opening through said handle means, said vent means being configured such that said gas conduit is substantially precluded from delivering gas to said longitudinal gas delivery lumen unless said vent means is closed, said gas conduit being disposed in said handle means and said vent means having a finger receiving portion for closing by a finger of the user; and means for providing controlled suction at said second end of said obturator means, said controlled suction means including a longitudinal suction lumen having two ends and being disposed in said elongated obturator means such that said lumen opens on one end thereof through said second end of said elongated obturator means, said other end of said longitudinal suction lumen being disposed adjacent to said handle means, and means for controlled delivery of suction to the other end of said longitudinal suction lumen, said controlled suction delivery means including a suction conduit having two ends and being in communication at one end thereof with the other end of said longitudinal suction lumen at the juncture of said handle means and said obturator means, said other end of said suction conduit for communicating with a suction apparatus, and suction vent means intermediate said ends of said suction conduit, said suction vent means being configured such that said suction conduit is substantially precluded from delivering suction to said suction lumen unless said suction vent means is closed, said suction conduit being disposed in said handle means and said suction vent means having an opening through said handle means for closing by a finger of the user;

wherein said trigger, said gas conduit vent means, and said suction vent means are controlled by the one hand of the user when said handle means is gripped by the one hand of the user.

19. A medical instrument for facilitating endotracheal intubation or the like in a patient by a selected endotracheal tube comprising:

handle means for gripping by one hand of a user;

an elongated obturator means having first and second ends and being fixedly secured adjacent to said first end thereof to said handle means, said obturator means for releasably retaining thereon a selected endotracheal tube, said obturator means having a longitudinal lumen disposed therein extending from said first end of said obturator means to said second end thereof, said obturator means also for removably receiving in said longitudinal lumen at least a portion of an endoscope thereby permitting visualization by said endoscope at said second end of said obturator means;

means for selectively retaining and ejecting the selected endotracheal tube when disposed upon said obturator means;

means for providing controlled delivery of a gas to said second end of said obturator means as desired by a user, said controlled gas delivery means including a longitudinal gas delivery lumen having two ends disposed in said elongated obturator means such that said longitudinal gas delivery lumen opens on one end thereof through said second end of said elongated obturator means, said other end of said longitudinal gas delivery lumen being disposed adjacent to said handle means, and means for controlled supply of gas to the other end of said longitudinal gas delivery lumen, said controlled gas supply means including a gas conduit disposed in said handle means, said gas conduit having two ends and being in communication at one end thereof with said other end of said longitudinal gas delivery lumen at the juncture of said handle means and said obturator means, the other end of said gas conduit for communicating with a supply of gas, and vent means intermediate said ends of said gas conduit and opening through said handle means, said vent means being configured such that said gas conduit is substantially precluded from delivering as to said longitudinal gas delivery lumen unless said vent means is closed; and means for providing controlled suction at said second end of said obturator means;

wherein said selectively retaining and ejecting means is selectable, and said controlled gas delivery means and said controlled suction means are each controllable by the one hand of the user when said handle means is gripped by said one hand of the user.

20. A medical instrument in accordance with claim 19, wherein said vent means is configured for closing by a finger of the user.

21. A medical instrument in accordance with claim 19, wherein said controlled suction means comprises a longitudinal suction lumen having two ends and being disposed in said elongated obturator means such that said lumen opens on one end thereof through said second end of said elongated obturator means, and means for controlled delivery of suction to the other end of said longitudinal suction lumen.

22. A medical instrument in accordance with claim 21, wherein said controlled suction delivery means comprises a suction conduit having two ends in communication atone end thereof with said other end of said longitudinal suction lumen at the juncture of said handle means and said obturator means, the other end of said suction conduit for communicating with a suction apparatus, and suction vent means intermediate said ends of said suction conduit, said suction vent means being configured such that said suction conduit is substantially precluded from delivering suction to said suction lumen unless said suction vent means is closed.

23. A medical instrument in accordance with claim 22, wherein said suction vent means opens through said handle means, said suction conduit being disposed in said handle means.

24. A medical instrument in accordance with claim 22, wherein said vent means and said suction vent means are adapted to be closed by the fingers of the user.

25. A medical instrument for facilitating endotracheal intubation or the like in a patient by a selected endotracheal tube comprising:

handle means to be gripped by one hand of a user;

elongated obturator means having first and second ends and being fixedly secured adjacent to said first end thereof to said handle means, said obturator means for releasably retaining thereon a selected endotracheal tube, said obturator means having a longitudinal lumen disposed therein extending from said first end of said obturator means to said second end thereof, said obturator means also for receiving therein at least a portion of an endoscope thereby permitting visualization by said endoscope at said second end of said obturator means;

means for selectively retaining and ejecting the selected endotracheal tube when disposed upon said obturator means;

means for providing controlled delivery of a gas to said second end of said obturator means; and means for providing controlled suction at said second end of said obturator means, said controlled suction means including a longitudinal suction lumen having two ends and being disposed in said elongated obturator means such that said lumen opens on one end thereof through said second end of said elongated obturator means, said other end of said longitudinal suction lumen being disposed adjacent to said handle means, and means for controlled delivery of suction to the other end of said longitudinal suction lumen, said controlled suction delivery means including a suction conduit disposed in said handle means, said suction conduit having two ends and being is communication at one end thereof with other end of said suction lumen, said other end of said suction conduit for communicating with a suction apparatus, and suction vent means intermediate said ends of said suction conduit and opening through said handle means, said suction vent means being configured such that said suction conduit is substantially precluded from delivering suction to said suction lumen unless said suction vent means is closed;

wherein said selectively retaining and ejecting means is selectable, and said controlled gas delivery means and said controlled suction means are each controllable by the one hand of the user when said handle means is gripped by the one hand of the user.

26. A medical instrument in accordance with claim 25, wherein said controlled gas delivery means comprises a longitudinal gas delivery lumen having two ends and being disposed in said elongated obturator means which opens on one end thereof through said second end of said elongated obturator means, and means for controlled supply of gas to the other end of said gas delivery lumen.

27. A medical instrument in accordance with claim 26, wherein said controlled gas supply means comprises a gas conduit having two ends and being in communication at one end thereof with said other end of said gas delivery lumen at the juncture of said handle means and said obturator means, the other end of said gas conduit for communicating with a supply of gas, and vent means intermediate said ends of said gas conduit, said vent means being configured such that said gas conduit is substantially precluded from delivering gas to said gas delivery lumen unless said vent means is closed.

28. A medical instrument in accordance with claim 27, wherein said gas conduit vent means opens through said handle means, said gas conduit being disposed in said handle means.

29. A medical instrument in accordance with claim 27, wherein said vent means is configured for closing by a finger of the user.

30. A medical instrument in accordance with claim 25, wherein said suction vent means is configured for closing by a finger of the user.

* * * * *